United States Patent [19]

Inagaki et al.

[11] Patent Number: 5,198,554
[45] Date of Patent: Mar. 30, 1993

[54] 5-(2,4-DIOXOTETRAHYDRO-3-FURANYL-METHYL)NORBORNANE-2,3-DICARBOXYLIC ACID ANHYDRIDE AND PROCESS FOR PRODUCTION THEREOF

[75] Inventors: Hiroyuki Inagaki, Kanagawa; Hiroshi Furukawa, Saitama; Takayoshi Kimura, Saitama; Hiroshi Ueno, Saitama, all of Japan

[73] Assignee: Tonen Corporation, Tokyo, Japan

[21] Appl. No.: 819,315

[22] Filed: Jan. 9, 1992

[30] Foreign Application Priority Data

Jan. 17, 1991 [JP] Japan .................................. 3-15763

[51] Int. Cl.⁵ .............................................. C07D 307/77
[52] U.S. Cl. ........................................ 549/237; 549/240
[58] Field of Search ................................ 549/239, 240

[56] References Cited

U.S. PATENT DOCUMENTS

| | | | |
|---|---|---|---|
| 3,996,249 | 12/1976 | Corson et al. | 549/240 |
| 4,144,244 | 3/1979 | Brace | 549/347 |
| 4,271,079 | 6/1981 | Maeda et al. | 549/240 |
| 4,273,719 | 6/1981 | Tani et al. | 549/240 |
| 4,371,688 | 2/1983 | Moore | 549/240 |
| 4,381,396 | 4/1983 | Ryang | 549/347 |
| 5,149,831 | 9/1992 | Furukawa et al. | 549/347 |

FOREIGN PATENT DOCUMENTS 9170086  9/1984  Japan .................................. 549/237

OTHER PUBLICATIONS

Maeda et al, CA93-133301r (1980).

*Primary Examiner*—Cecilia Tsang
*Attorney, Agent, or Firm*—J. J. Mahon

[57] ABSTRACT

A novel compound 5-(2,4-dioxotetrahydro-3-furanylmethyl)norbornane-2,3-dicarboxylic acid anhydride has been provided. The compound is prepared by hydrogenating 5-(2,4-dioxotetrahydro-3-furanylmethyl)-5-norbornene-2,3-di-carboxylic acid anhydride. The compound may be used as a hardening agent for epoxy resins, a raw material of producing polyimides, polyamides and polyesters, and a raw material for a plasticizer for vinyl chloride polymers.

1 Claim, No Drawings

5-(2,4-DIOXOTETRAHYDRO-3-FURANYLMETHYL)NORBORNANE-2,3-DICARBOXYLIC ACID ANHYDRIDE AND PROCESS FOR PRODUCTION THEREOF

The present invention relates to a novel tetracarboxylic acid anhydride which is useful as an epoxy resin hardening agent and the like, as well as to methods of preparing it.

In general, tetracarboxylic acid anhydrides are used as an epoxy resin hardening agent for the purpose of obtaining a heat-resistant hardened product, a raw material for polyimide resins, a raw material for a plasticizer for vinyl chloride resins, and a raw material for water-soluble polyesters, and the field of utilizing them is broad.

Hitherto, as an epoxy resin hardening agent, there have been used pyromellitic acid dianhydride, benzophenonetetracarboxylic acid dianhydride, methylcyclohexenetetracarboxylic acid dianhydride and the like. However, the former two of pyromellitic acid dianhydride and benzophenonetetracarboxylic acid dianhydride are poorly compatible with epoxy resins. In addition, since they begin to harden epoxy resins immediately after they are dissolved in the resins, the pot life of them is short. Therefore, they have a drawback that they cannot be used for casting compositions unless they are not blended with maleic anhydride. The last one of methylcyclohexenetetracarboxylic acid dianhydride is free from the drawback, but it has a high melting point of about 168° C. so that the workability of it is poor. In addition, they are all high-priced.

The object of the present invention is to provide a low-priced tetracarboxylic acid dianhydride, which is free from the above-mentioned drawbacks in the prior art and has a good workability, and to provide a method of preparing it.

First, the present invention provides a tetracarboxylic acid dianhydride which is 5-(2,4-dioxotetrahydro-3-furanylmethyl)norbornane-2,3-dicarboxylic acid anhydride of a chemical formula:

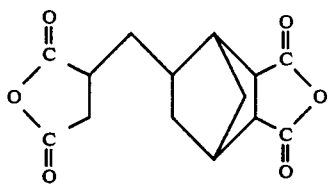

The compound of the present invention has a low melting point and therefore has a good workability. In addition, it is highly compatible with epoxy resins so that it can be used singly as a hardening agent even in casting of epoxy resins. Moreover, the thus hardened epoxy resin products have a heat resistance comparable to those as hardened with the conventional tetracarboxylic acid dianhydrides. The compound of the present invention can also be used as a raw material for polyimides, polyamides and polyester resins, and as a raw material for a plasticizer for vinyl chloride polymers. Thus, the technical field to which the compound of the invention is applied is broad.

Secondly, the present invention provides a method of preparing the above-mentioned compound.

Specifically, the compound of the present invention can easily be prepared by hydrogenating 5-(2,4-dioxotetrahydro-3-furanylmethyl)-5-norbornene-2,3-dicarboxylic acid anhydride.

5-(2,4-Dioxotetrahydro-3-furanylmethyl)-5-norbornene-2,3-dicarboxylic acid anhydride itself is a novel substance and is useful also as an epoxy resin hardening agent like the compound of the present invention. The compound is prepared by reacting 5-methylenenorbornane-2,3-dicarboxylic acid anhydride, or 1-methylnorbornene-2,3-dicarboxylic acid anhydride and/or 5-methylnorbornene-2,3-dicarboxylic acid anhydride, with maleic anhydride.

5-Methylenenorbornane-2,3-dicarboxylic acid anhydride which is one starting material has a double bond at the terminal thereof and is therefore extremely highly reactive to easily react with maleic anhydride to give 5-(2,4-dioxotetrahydro-3-furanylmethyl)-5-norbornene-2,3-dicarboxylic acid anhydride. The reaction is presumed to proceed as mentioned below. This is ene-production of a kind, and such ene-production of itself is described in, for example, Japanese Patent Publication No. 58-51955.

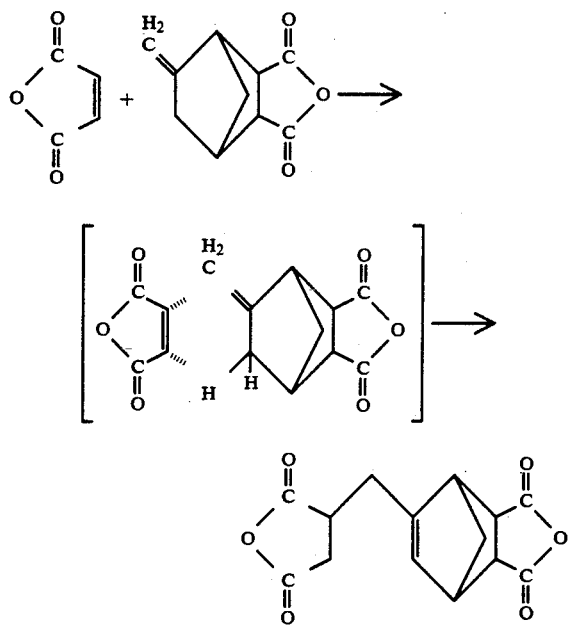

For effecting the reaction, in general, 5-methylenenorbornane-2,3-dicarboxylic acid anhydride and maleic anhydride are fed into a reactor in a molar ratio of from 0.5/1 to 5/1 and are heated preferably at a temperature of approximately from 160° to 220° C. for approximately from 2 to 24 hours with stirring. The reaction may be effected in the presence of any desired catalyst. As a usable catalyst, Lewis acids such as aluminium chloride or boron fluoride are preferred, which, however, are not limitative. The reaction does not need a solvent, but may be effected in any desired solvent. As preferred solvents, there are mentioned chlorobenzene, xylene, mesitylene, triethylbenzene, etc.

5-Methylenenorbornane-2,3-dicarboxylic acid anhydride can be prepared by isomerizing 1-methylnorbornene-2,3-dicarboxylic acid anhydride and/or 5-methylnorbornene-2,3-dicarboxylic acid anhydride in the presence of an acid catalyst. "Isomerization" as referred to herein broadly includes structural isomerization and stereoisomerization but does not have a narrow meaning of geometric isomerization and position isomerization. 5-Methylenenorbornane-2,3-dicarboxylic acid anhydride includes to stereoisomers of endo form and exo form, and the present invention may use any of them. A mixture of the two may also be used.

1-Methylnorbornene-2,3-dicarboxylic acid anhydride and 5-methylnorbornene-2,3-dicarboxylic acid anhydride (hereinafter referred to as "1-MeNA" and "5-MeNA", respectively) of themselves are known. Both of the two acid anhydrides each have two stereoisomers of endo form and exo form, and both of the two stereoisomers can be used in the present invention.

The starting compounds of 1-MeNA and 5-MeNA can be produced, for example, as follows: Precisely, 1-methylcyclopentadiene (hereinafter referred to as "1-MeCPD") and 2-methylcyclopentadiene (hereinafter referred to as "2MeCPD") are reacted with maleic anhydride (Diels-Alder reaction) to produce endo-1-MeNA from 1-MeCPD and endo-5-MeNA from 2-MeCPD. 1-MeCPD and 2-MeCPD are available generally as a mixture of them, and it is unnecessary to isolate the two from each other for the purpose of the invention.

The thus obtained mixture of 1-MeNA and 5-MeNA is isomerized in the manner as will be mentioned below, whereby endo-1-MeNA gives exo-5-methylenenorbornane-2,3-dicarboxylic acid anhydride via exo-5-MeNA, while endo-5-MeNA directly gives endo-5-methylenenorbornane-2,3-dicarboxylic anhydride. A part of endo-5-MeNA may give exo-5-methylenenorbornane-2,3-dicarboxylic acid anhydride via exo-5-MeNA. Where endo1MeNA is heated in the absence of an acid in the manner as will be mentioned below, it could be isomerized into exo-5-MeNA but is not isomerized further into exo-5-methylenenorbornane-2,3-dicarboxylic acid anhydride.

Methylnorbornene-2,3-dicarboxylic acid anhydride is available as a commercial product, and it may be used in the present invention.

Isomerization may be effected by heating 1-methylnorbornene-2,3-dicarboxylic acid anhydride and/or 5-methylnorbornene-2,3-dicarboxylic acid anhydride in the presence of an acid. Acids to be used for the isomerization are not specifically defined but various known acids can be used. For instance, as usable acids, there are mentioned Bronsted acids, for example, aromatic sulfonic acids such as benzenesulfonic acid, paratoluenesulfonic acid and paraxylene-2-sulfonic acids, mineral acids such as sulfuric acid and hydrochloric acid, hetero-polyacids such as molybdic acid, and carboxylic acids such as maleic acid; as well as other Lewis acids such as aluminium chloride or boron fluoride. Since acid anhydrides such as maleic anhydride may be reacted with water to give the corresponding acids, they may also be used in place of acids to carry out the isomerization. In the present invention, use of Bronsted acids is preferred. The amount of the acid to be used in the reaction is preferably approximately from 0.01 to 5% by weight, especially preferably approximately from 0.02 to 3% by weight, to the methylnorbornene-2,3-dicarboxylic acid anhydride to be reacted. The temperature for heating is preferably approximately from 120° to 250° C., especially preferably approximately from 150° to 230° C. The isomerization under heat can be effected either by a batchwise system or a continuous system. The reaction time is preferably approximately from 30 minutes to 10 hours, especially preferably approximately from 1 to 5 hours for batchwise reaction.

The 5-methylenenorbornane-2,3-dicarboxylic acid anhydride thus obtained by the method mentioned above is then reacted with maleic anhydride in the manner as mentioned above, to thereby obtain 5-(2,4-dioxotetrahydro-3-furanylmethyl)-5-norbornene-2,3-dicarboxylic acid anhydride. Apart from this, the above-mentioned isomerization and ene-production can be effected as one operation. Briefly, 1-methylnorbornene-2,3-dicarboxylic acid anhydride and/or 5-methylnorbornene-2,3-dicarboxylic acid anhydride are/is heated in the presence of maleic anhydride to give 5-(2,4-dioxotetrahydro-3-furanylmethyl)-5-norbornene-2,3-dicarboxylic acid anhydride via successive isomerization and ene-production.

After the above-mentioned reaction, the product is preferably purified prior to hydrogenation thereof. Purification of the product may be effected by removing the non-reacted raw materials by simple distillation or the like followed by recrystallization of the obtained crude product. As solvents usable for the recrystallization, there are mentioned acetic anhydride and ketone solvents such as methyl isobutyl ketone and the like, which, however, are not limitative.

The 5-(2,4-dioxotetrahydro-3-furanylmethyl)-5-norbornene-2,3-dicarboxylic acid anhydride thus obtained is hydrogenated to obtain the compound of the present invention.

Hydrogenation for obtaining the compound of the invention is not specifically defined but may be effected by various known methods. For instance, there are mentioned a method of catalytic hydrogenation of 5-(2,4-dioxotetrahydro-3-furanylmethyl)-5-norbornene-2,3-dicarboxylic acid anhydride, and a method of applying a combination of hydrogen iodide and red phosphorus or a combination of sodium and alcohol to the acid anhydride. However, these methods are not limitative. Preferred is the former catalytic hydrogenation. In general, the catalytic hydrogenation is effected by bringing 5-(2,4-dioxotetrahydro-3-furanylmethyl)-5-norbornene-2,3-dicarboxylic acid anhydride into contact with hydrogen under heat, preferably in the presence of a hydrogenation catalyst. As preferred hydrogenation catalysts for the process, there are mentioned palladium, cobalt, nickel, platinum and the like, which, however, are not limitative. The catalyst may be in the form with a carrier. The heating temperature is preferably approximately from 80° to 300° C., more preferably approximately from 120° to 250° C. The hydrogen pressure during the hydrogenation reaction is preferably approximately from 10 to 150 kg/cm$^2$G. The reaction time is preferably approximately from 1 to 10 hours, more preferably from 2 to 6 hours. No solvent is necessary in the hydrogenation. However, since the starting materials and the product are solid at room temperature and in order to smoothly conduct the hydrogenation, a solvent such as tetrahydrofuran or the like may be in the reaction system.

It is also possible to hydrogenate the 5-(2,4-dioxotetrahydro-3-furanylmethyl)-5-norbornene-2,3-dicarboxylic acid anhydride as obtained by the above-mentioned production method, without isolation or after simple purification, to obtain the intended product of the present invention.

After the above-mentioned reaction, the product may be purified. Purification of the product may be effected by recrystallization with a solvent such as methyl isobutyl ketone.

The compound of the present invention can be identified by various determination means such as IR, NMR, etc. For instance, in IR of the compound, there are seen peaks at 1770 to 1780 cm$^{-1}$ and at 1850 cm$^{-1}$ to be caused by stretching vibration of C=O of the carboxylic acid anhydride moiety. In $_1$H-NMR of the same, there are seen peaks 8H's to be caused by four —CH$_2$—'s at δ1.8 to 2.4 (only peaks 6H's are seen in the starting substance 5-(2,4-dioxotetrahydro-3-furanylmethyl)-5-norbornene-2,3-dicarboxylic acid anhydride; only peaks 4H's in 5-methylenenorbornane-2,3-dicarboxylic acid anhydride; and only peaks 2H's in 1- or 5-methylnorbornene-2,3-dicarboxylic acid anhydride); and there are seen peaks 6H's to be caused by six <CH—'s at 82.0 to 3.6 (only peaks 5H's are seen in the starting substance 5-(2,4-dioxotetrahydro-3-furanylmethyl)-5-norbornene-2,3-dicarboxylic acid anhydride; only peaks 4H's in 5-methylenenorbornane-2,3-dicarboxylic acid anhydride and 5-methylnorbornene-2,3-dicarboxylic acid anhydride; and only peaks 3H's in 1-methylnorbornene-2,3-dicarboxylic acid anhydride). On the other hand, peaks at δ5.5 to 5.6 to be caused by =CH— in norbornene ring moiety (a peak 1H is seen in the starting substance 5-(2,4-dioxotetrahydro-3furanylmethyl)-5-norbornene-2,3-dicarboxylic acid anhydride and 5-methylnorbornene-2,3-dicarboxylic acid anhydride; peaks 2H's in 1-methylnorbornene-2,3-dicarboxylic acid anhydride); peaks of vinylidene (peaks 2H's are seen in the starting substance 5-methylenenorbornane-2,3-dicarboxylic acid anhydride); and peaks of methyl group (peaks 3H's are seen in the starting substance 1- or 5-methylnorbornene-2,3-dicarboxylic acid anhydride) are not seen in $^1$H-NMR of the product.

Next, the present invention will be explained in more detail by way of the following examples, which do not whatsoever restrict the scope of the present invention.

Unless otherwise specifically indicated, all "%" and "parts" in the following examples are by weight.

EXAMPLE 1

300 g of endo-methylnorbornene-2,3-dicarboxylic acid anhydride (comprising 58.5% of 1-methyl form and 41.5% of 5-methyl form) and 0.15 g of paratoluenesulfonic acid were introduced into a 500 ml four-neck flask equipped with a reflux condenser, a thermometer and a stirrer, and they were reacted with stirring at 180° C. for 3 hours. By simple distillation of the reaction mixture, 287 g of a pale yellow transparent liquid, as separated from the catalyst and heavy by-products, was obtained. The composition of the liquid was analyzed by gas chromatography, which was clarified to comprise 8.8% of endo-5-methylenenorbornane-2,3-dicarboxylic acid anhydride, 63.5% of exo-5-methylenenorbornane-2,3-dicarboxylic acid anhydride and 27.7% of the non-reacted methylnorbornene-2,3-dicarboxylic acid anhydride. The structure of the product was identified by infrared absorption spectrography (IR) and $^1$H-NMR. For instance, in IR of the product, there were seen peaks to be caused by stretching vibration of C=O of the carboxylic acid anhydride moiety at 1770 to 1780 cm$^{-1}$ and at 1850 cm$^{-1}$. In $^1$H-NMR Of the same, peaks to be caused by H$_2$C=C< (which were not seen in the starting substance methylnorbornene-2,3-dicarboxylic acid anhydride) were seen at δ4.8 to 5.2; peaks 4H's to be caused by —CH$_2$— (these are 2H's in the starting substance) were seen at δ1.8; and peaks to be caused by protons as bonded to the tertiary carbon atoms of the norbornane ring moiety were seen at δ2.8 to 3.6. No peak to be caused by =CH— of norbornene ring was seen.

Next, 270 g of the pale yellow transparent liquid as obtained in the above-mentioned process and 294 g of maleic anhydride were put in a 1000 ml four-neck flask as equipped with a reflux condenser, a thermometer and a stirrer, and stirred for 6 hours at 180° C. Next, the reaction system was subjected to simple distillation under a reduced pressure of 5 mmHg until the temperature of the bath became 180° C., whereby the non-reacted 5-methylenenorbornane-2,3-dicarboxylic acid anhydride, methylnorbornene-2,3-dicarboxylic acid anhydride and maleic anhydride were removed. As a result, 126 g of a product was obtained.

The structure of the compound obtained was identified by infrared absorption spectrography (IR) and $^1$-NMR. For instance, in IR of the compound, peaks to be caused by stretching vibration of C=O of the carboxylic acid anhydride were seen at 1770 to 1780 cm$^{-1}$ and at 1850 cm$^{-1}$. In $^1$H-NMR of the same, there were seen peaks 6H's to be caused by three —CH$_2$—'s at δ1.8 to 2.2 (only peaks 2H's were seen in the starting substance 1- or 5-methylnorbornene-2,3-dicarboxylic acid anhydride; and only peaks 4H's in 5-methylenenorbornane-2,3-dicarboxylic acid anhydride); there were seen peaks 5H's to be caused by five >CH—'s at δ2.8 to 3.6 (only peaks 4H's were seen in the starting substance 5-methylenenorbornane-2,3-dicarboxylic acid anhydride and 5-methylnorbornene-2,3-dicarboxylic acid anhydride; and only peaks 3H's in 1-methylnorbornene-2,3-dicarboxylic acid anhydride); and were seen a peak 1H to be caused by =C—H— of norbornene ring moiety at δ5.5 to 5.6; while there were seen neither peak or methyl group moiety (peaks 3H's to be caused by methyl group moiety were seen in the starting substance 1- or 5-methylnorbornene-2,3-dicarboxylic acid anhydride) nor peak to be caused by vinylidene group moiety (peaks 2H's to b caused by vinylidene group moiety were seen in the starting substance 5-methylenenorbornane-2,3-dicarboxylic acid anhydride). From these results, the product was identified to be 5-(2,4-dioxotetrahydro-3-furanylmethyl)-5-norbornene-2,3-dicarboxylic acid anhydride.

120 g of the product obtained by the above-mentioned process, 2.4 g of a palladium catalyst (carrying 5 wt. % palladium metal) and 120 g of tetrahydrofuran as a solvent were put in a 500 ml-autoclave as equipped with a stirrer, and the inside of the autoclave was substituted by hydrogen and then heated up to 120° C. under hydrogen pressure of 80 kg/cm$^2$G whereupon the compound in the autoclave was hydrogenated for 4 hours with stirring. After completion of reaction, the catalyst was removed by filtration under reduced pressure and the residue was then gradually heated up to 150° to 170° C. under normal pressure (this is because the residue is solidified if not heated) and subjected to distillation under normal pressure. After the solvent of tetrahydrofuran was completely removed therefrom by distillation under reduced pressure, 112 g of a product was obtained.

The results of analysis of the product are shown in Table 1 below.

TABLE 1

| Item | Date | Identification or Theoretical Value |
|---|---|---|
| IR | 1770 to 1780 cm$^{-1}$ 1850 cm$^{-1}$ | Stretching vibration of C = O in carboxylic |

TABLE 1-continued

| Item | Date | Identification or Theoretical Value |
|---|---|---|
| | | acid anhydride moiety |
| 1H-NMR* | 1.8 to 2.4 (8H) | $-C\underline{H}_2$-(8H) |
| | 2.0 to 3.6 (6H) | $>C\underline{H}$-(6H) |
| Neutralization Value | 760 | 803 |
| Iodine Value | 2.6 | 0 |

*— (unit, ppm): The parenthesized value indicates the number of protons corresponding to the integrated intensity.

From the above-mentioned data, the product obtained in the present example was identified to be the compound of the present invention being 5-(2,4-dioxotetrahydro-3furanylmethyl)norbornane-2,3-dicarboxylic acid anhydride. The iodine value of the non-hydrogenated compound of 5-(2,4-dioxotetrahydro-3-furanylmethyl)-5-norbornene-2,3-dicarboxylic acid anhydride was 88.2. Reduction of the iodine value of the hydrogenated product to be 2.6 well supports the conclusion.

USE EXAMPLE 70 parts of the compound obtained in the previous example [5-(2,4-dioxotetrahydro-3-furanylmethyl)norbornane-2,3-dicarboxylic acid anhydride] and 100 parts of an epoxy resin (Epikote 828 (trade name), product by Yuka Shell Co.) were blended at 140° C. and then cooled to 80° C. One part of dimethylbenzylamine was added thereto and blended, and the resulting mixture was cast into a casting frame. After hardened at 160° C. for 15 hours, the thermal deformation temperature of the hardened product was measured in accordance with JIS K 6911, which was 186° C.

COMPARATIVE USE EXAMPLE 1

50 parts of benzophenonetetracarboxylic acid dianhydride and 100 parts of an epoxy resin (Epikote 828 (trade name), product by Yuka Shell Co.) were intended to be blended at 140° C. to fail in forming a uniform blend. Then, the system was gradually heated with continuously stirring, and it gave a uniform layer at a temperature of 170° C. but it soon gelled.

COMPARATIVE USE EXAMPLE 2

60 parts of methylcyclohexenetetracarboxylic acid dianhydride (Epikuron B-4400 (trade name), product by Dai-Nippon Ink Co.) and 100 parts of an epoxy resin (Epikote 828 (trade name), product by Yuka Shell Co.) were blended at 140° C. and then cooled to 80° C. One part of dimethylbenzylamine was added thereto and blended, and the resulting blend was hardened under the same condition as that in Use Example 1 and the thermal deformation temperature of the hardened product was measured to be 169° C.

Referential Use Example 70 parts of the intermediate obtained in the previous example [5-(2,4-dioxotetrahydro-3-furanylmethyl)-5-norbornene-2,3-dicarboxylic acid anhydride] and 100 parts of an epoxy resin (Epikote 828 (trade name), product by Yuka Shell Co.) were blended at 120° C. and then cooled to 80° C. One part of dimethylbenzylamine was added thereto and blended and the resulting blend was cast into a casting frame. After hardened for 15 hours at 160° C., the thermal deformation temperature of the hardened product was measured to be 176° C.

From the results of Use Example and Comparative Use Examples 1 and 2, it is understood that the compound of the present invention may be blended with an epoxy resin and may be processed more easily than the conventional epoxy resin hardening agents. In addition, the epoxy resin as hardened with the compound of the present invention is noted to have a higher thermal deformation temperature than that as hardened with the conventional hardening agent.

Advantage of the Invention

In accordance with the present invention, there are provided a novel compound 5-(2,4-dioxotetrahydro-3-furanylmethyl)norbornane-2,3-dicarboxylic acid anhydride and a method of producing it. The compound has a low melting point and has a good workability. In addition, since it is well compatible with epoxy resins, it can be used singly as a hardening agent in casting of epoxy resins. Moreover, the epoxy resin articles as hardened with the compound of the invention have a higher heat resistance than those as hardened with any other conventional tetracarboxylic acid dianhydrides having a poorer workability. Therefore, the compound of the present invention can be used as a hardening agent for epoxy resin sealants for electronic parts or electric parts which are to be large scale integration circuits and which are desired to have a high heat resistance. In addition, the compound of the present invention can also be used as a raw material for producing polyimides, polyamides and polyesters and as a raw material for a plasticizer for vinyl chloride polymers. The technical field to which the compound of the present invention is applied is broad.

What is claimed:

1. 5-(2,4-Dioxotetrahydro-3-furanylmethyl)norbornane-2,3-dicarboxylic acid anhydride of the chemical formula:

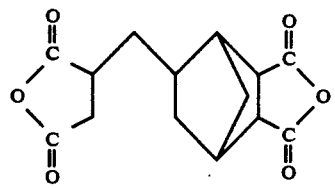

* * * * *